(12) United States Patent
Morse et al.

(10) Patent No.: US 10,869,951 B2
(45) Date of Patent: *Dec. 22, 2020

(54) TISSUE GRAFTS MODIFIED WITH A CROSS-LINKING AGENT AND METHOD OF MAKING AND USING THE SAME

(71) Applicant: MiMedx Group, Inc., Marietta, GA (US)

(72) Inventors: Brenda S. Morse, Marietta, GA (US); Somaly Sith, Marietta, GA (US); Randall Spencer, Marietta, GA (US); John Daniel, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 43 days.

This patent is subject to a terminal disclaimer.

(21) Appl. No.: 16/260,733

(22) Filed: Jan. 29, 2019

(65) Prior Publication Data

US 2019/0192736 A1    Jun. 27, 2019

Related U.S. Application Data

(60) Division of application No. 15/074,949, filed on Mar. 18, 2016, now Pat. No. 10,232,085, which is a continuation of application No. 13/984,842, filed as application No. PCT/US2012/024814 on Feb. 13, 2012, now abandoned.

(60) Provisional application No. 61/442,348, filed on Feb. 14, 2011.

(51) Int. Cl.
  *A61L 27/36* (2006.01)
  *A61K 35/50* (2015.01)

(52) U.S. Cl.
  CPC .......... *A61L 27/3604* (2013.01); *A61K 35/50* (2013.01); *A61L 27/3687* (2013.01); *A61L 2430/40* (2013.01)

(58) Field of Classification Search
  None
  See application file for complete search history.

(56) References Cited

U.S. PATENT DOCUMENTS

| | | | |
|---|---|---|---|
| 2,694,914 | A | 11/1954 | Glover, Jr. |
| 4,361,552 | A | 11/1982 | Baur, Jr. |
| 4,564,368 | A | 1/1986 | Sawyer et al. |
| 4,745,771 | A | 5/1988 | Linner et al. |
| 4,968,325 | A | 11/1990 | Black et al. |
| 4,971,954 | A | 11/1990 | Brodsky et al. |
| 5,118,867 | A | 6/1992 | Bahrmann et al. |
| 5,284,655 | A | 2/1994 | Bogdansky et al. |
| 6,030,635 | A | 2/2000 | Gertzman et al. |
| 6,682,760 | B2 | 1/2004 | Noff et al. |
| 6,893,462 | B2 | 5/2005 | Buskirk et al. |
| 7,101,857 | B2 | 9/2006 | Sung et al. |
| 7,311,904 | B2 | 12/2007 | Hariri |
| 7,311,905 | B2 | 12/2007 | Hariri |
| 8,067,044 | B2 | 11/2011 | Henry et al. |
| 8,153,162 | B2 | 4/2012 | Tseng et al. |
| 8,323,701 | B2 | 12/2012 | Daniel et al. |
| 8,357,403 | B2 | 1/2013 | Daniel et al. |
| 8,372,439 | B2 | 2/2013 | Daniel et al. |
| 8,904,664 | B2 | 12/2014 | Pringle et al. |
| 9,180,145 | B2 | 11/2015 | Brown et al. |
| 2001/0053839 | A1 | 12/2001 | Noishiki et al. |
| 2002/0019516 | A1 | 2/2002 | Noff et al. |
| 2002/0123141 | A1 | 9/2002 | Hariri |
| 2002/0160510 | A1 | 10/2002 | Hariri |
| 2003/0032179 | A1 | 2/2003 | Hariri |
| 2003/0143207 | A1 | 7/2003 | Livesey et al. |
| 2003/0187515 | A1 | 10/2003 | Hariri et al. |
| 2004/0048796 | A1 | 3/2004 | Hariri et al. |
| 2006/0140913 | A1 | 6/2006 | Bhatia |
| 2006/0210532 | A1 | 9/2006 | Carmeliet et al. |
| 2007/0021762 | A1 | 1/2007 | Liu et al. |
| 2007/0202189 | A1 | 8/2007 | Ahlfors |
| 2007/0248575 | A1 | 10/2007 | Connor et al. |
| 2007/0299043 | A1 | 12/2007 | Hunter et al. |
| 2008/0046095 | A1 | 2/2008 | Daniel |
| 2008/0050347 | A1 | 2/2008 | Ichim |
| 2008/0069895 | A1 | 3/2008 | Liu et al. |
| 2008/0131966 | A1 | 6/2008 | Hariri |
| 2008/0181967 | A1 | 7/2008 | Liu et al. |
| 2008/0233552 | A1 | 9/2008 | Ma et al. |

(Continued)

FOREIGN PATENT DOCUMENTS

| | | |
|---|---|---|
| EP | 0431479 A1 | 6/1991 |
| JP | H07-213597 | 8/1995 |

(Continued)

OTHER PUBLICATIONS

Office Action for Korean Application No. 10-2013-7023861 dated Feb. 15, 2019.

(Continued)

*Primary Examiner* — Allison M Fox
(74) *Attorney, Agent, or Firm* — Alston & Bird LLP

(57) ABSTRACT

Described herein are tissue grafts derived from the placenta that possess good adhesion to biological tissues and are useful in would healing applications. In one aspect, the tissue graft includes (1) two or more layers of amnion, wherein at least one layer of amnion is cross-linked, (2) two or more layers of chorion, wherein at least one layer of amnion is cross-linked, or (3) one or more layers of amnion and chorion, wherein at least one layer of amnion and/or chorion is cross-linked. In another aspect, the grafts are composed of amnion and chorion cross-linked with one another. In a further aspect, the grafts have one or more layers sandwiched between the amnion and chorion membranes. The amnion and/or the chorion are treated with a cross-linking agent prior to the formation of the graft. The presence of the cross-linking agent present on the graft also enhances adhesion to the biological tissue of interest. Also described herein are methods for making and using the tissue grafts.

20 Claims, 3 Drawing Sheets

(56) References Cited

U.S. PATENT DOCUMENTS

| | | |
|---|---|---|
| 2009/0012629 A1 | 1/2009 | Yao et al. |
| 2009/0142831 A1 | 6/2009 | Hariri |
| 2009/0291891 A1 | 11/2009 | Neufeld |
| 2010/0028849 A1 | 2/2010 | Shelby et al. |
| 2010/0104539 A1 | 4/2010 | Daniel et al. |
| 2010/0136114 A1 | 6/2010 | Mao |
| 2010/0143312 A1 | 6/2010 | Hariri et al. |
| 2010/0178297 A1 | 7/2010 | Carmeliet et al. |
| 2010/0209408 A1 | 8/2010 | Livesey et al. |
| 2010/0260847 A1 | 10/2010 | Hariri |
| 2010/0272782 A1 | 10/2010 | Owens et al. |
| 2011/0044997 A1 | 2/2011 | Rankin et al. |
| 2011/0177150 A1 | 7/2011 | Pathak et al. |
| 2011/0189301 A1 | 8/2011 | Yang et al. |
| 2011/0307059 A1 | 12/2011 | Young et al. |
| 2012/0010708 A1 | 1/2012 | Young et al. |
| 2012/0030963 A1 | 2/2012 | Durance et al. |
| 2012/0078378 A1 | 3/2012 | Daniel et al. |
| 2012/0083900 A1 | 4/2012 | Samaniego et al. |
| 2013/0202676 A1 | 8/2013 | Koob et al. |
| 2013/0218274 A1 | 8/2013 | Spencer et al. |
| 2013/0230561 A1 | 9/2013 | Daniel et al. |
| 2013/0344162 A1 | 12/2013 | Morse et al. |
| 2014/0017280 A1 | 1/2014 | Daniel et al. |
| 2014/0052247 A1 | 2/2014 | Daniel et al. |
| 2014/0052274 A1 | 2/2014 | Koob et al. |
| 2014/0067058 A1 | 3/2014 | Koob et al. |
| 2014/0106447 A1 | 4/2014 | Brown et al. |
| 2014/0205646 A1 | 7/2014 | Morse et al. |
| 2014/0271728 A1 | 9/2014 | Koob et al. |

FOREIGN PATENT DOCUMENTS

| | | |
|---|---|---|
| JP | 2004-515451 | 5/2004 |
| JP | 2006-507851 | 3/2006 |
| JP | 2006-230749 | 9/2006 |
| KR | 10/1991/0011272 | 8/1991 |
| KR | 10/1991/0011727 | 8/1991 |
| KR | 10-0999247 | 12/2010 |
| WO | WO-93/10722 | 6/1993 |
| WO | WO-01/08716 A1 | 2/2001 |
| WO | WO 2001/079342 | 10/2001 |
| WO | WO-2005/007835 A1 | 1/2005 |
| WO | WO-2005/017165 A1 | 2/2005 |
| WO | WO-2009/033160 A1 | 3/2009 |
| WO | WO-2009/048908 A1 | 4/2009 |
| WO | WO-2009/132186 A1 | 10/2009 |
| WO | WO-2010/029344 A2 | 3/2010 |
| WO | WO-2012/003377 | 1/2012 |
| WO | WO-2012/069559 A1 | 5/2012 |
| WO | WO-2012/112410 A2 | 8/2012 |
| WO | WO-2012/112417 A2 | 8/2012 |
| WO | WO-2012/112441 A1 | 8/2012 |
| WO | WO-2013/095830 A1 | 6/2013 |

OTHER PUBLICATIONS

Autiero et al., "Placental growth factor and its receptor, vascular endothelial growth factor receptor-1:novel targets for stimulation of ischemic tissue revascularization and inhibition of angiogenic and inflammatory disorders," J. Thromb. Haerno., (2003), 1:1356-1370.
EpiFix Product Brochure (2011).
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
International Preliminary Report on Patentability dated Dec. 8, 2014 for International Patent Application No. PCT/US2013/054325.
Kelly et al., "Disparate Effects of Similar Phenolic Phytocheinicals as Inhibitors of Oxidative Damage to Cellular DNA", Mutation Res., vol. 485, pp. 309-318, (2001).
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Koob et al., "Biological properties of dehydrated human amnion chorion composite graft: implications for chronic wound healing", International Wound Healing, 2013, 10(5):493-500.
Lu et al., "Molecular mechanisms and clinical applications of nordihydroguaiaretic acid (NDGA) and its derivatives: An update," Med. Sci. Monit., (2010), 16(5):RA93-RA100.
Mayfield et al., "Waterlight closure of spinal dura mater: Technical note," J. Neurosurg., (1975), 43(5):639-640.
"MiMedx Group Announces Launch of EpiFixTM and Hiring of Vice President, Wound Care," Mimedx Press Release (2011).
MiMedx Press Release, "MiMedx Scientific Study is Electronically Published in the International Wound Journal", 2013.
Moussy et al., "Transport characteristics of a novel local drug delivery system using nordihydroguaiaretic acid (NDGA)-polymerized collagen fibers," Biotechnology Progress, (2007), 23(4):990-994.
PCT International Preliminary Report on Patentability dated Feb. 14, 2013 for PCT Patent Application No. PCT/US2012/024814.
International Preliminary Report on Patentability for International Patent Application No. PCT/US2013/054319 dated Nov. 28, 2014.
PCT International Preliminary Report on Patentability dated Jan. 16, 2014 in related PCT Patent Application No. PCT/US12/66862.
PCT International Preliminary Report on Patentability for PCT Application No. PCT/US2012/024798, dated Feb. 1, 2013.
PCT International Search Report and Written Opinion for PCT Application No. PCT/US2012/065672 dated Feb. 8, 2013.
PCT International Search Report and Written Opinion for PCT Patent Application No. PCT/US2012/024814 dated Aug. 16, 2012.
PCT International Search Report and Written Opinion for PCT Patent Application No. PCT/US2012/065672 dated Feb. 8, 2013.
PCT International Search Report and Written Opinion for PCT Application No. PCT/US2013/054322 dated Oct. 22, 2013.
PCT International Search Report and Written Opinion for copending PCT Application No. PCT/US2012/66862, dated Feb. 12, 2013.
PCT International Search Report and Written Opinion for copending PCT Application No. PCT/US2013/054319, dated Nov. 13, 2013.
PCT International Search Report and Written Opinion for copending PCT Application No. PCT/US2013/054320, dated Nov. 6, 2013.
PCT International Search Report and Written Opinion for copending PCT Application No. PCT/US2013/054325, dated Oct. 28, 2013.
PCT International Search Report and Written Opinion for copending PCT Application No. PCT/US2013/055003, dated Nov. 19, 2013.
PCT International Search Report and Written Opinion for copending PCT Appl. PCT/US2013/064146, dated Jan. 9, 2014.
PCT International Search Report and Written Opinion for copending PCT Application No. PCT/US2012/024798, dated Jun. 20, 2012.
Supplementary European Search Report for Application No. EP 12746488,1 dated Oct. 6, 2015.
Uchide, N., et al,, "Possible Role of Proinflammatory and Chemoattractive Cytokines Produced by Human Fetal Membrane Celss in the Pathology of Adverse Preganancy Outcomes Associated with Influenza Virus Infection," Mediators of Inflammation, 2012: 1-32 (2012).
Tao, et al., "Implantation of amniotic membrane to reduce postlaminectomy epiduria adhesions" Eur. Spine. J., (2009) 18:1202-1212.
Office Action for European Application No. 12746488.1 dated Jan. 31, 2019, 6 pages.

TISSUE GRAFTS MODIFIED WITH A CROSS-LINKING AGENT AND METHOD OF MAKING AND USING THE SAME

CROSS-REFERENCE TO RELATED APPLICATIONS

This application is a divisional of U.S. patent application Ser. No. 15/074,949, filed Mar. 18, 2016, which is a Continuation Application of U.S. patent application Ser. No. 13/984,842, filed Mar. 14, 2014, which is a National Stage entry of International Application No. PCT/US2012/024814, filed Feb. 13, 2012, which claims priority upon U.S. provisional application Ser. No. 61/442,348, filed Feb. 14, 2011, each of which are hereby incorporated by reference in their entirety for all of their teachings.

BACKGROUND

The human spinal cord and brain are covered with the meninges membranes, consisting of three overlapping layers of tissue including the outermost dura mater, arachnoid mater and innermost pia mater. The meningeal membranes are critical to the operation of the central nervous system and their disruption, by accident or surgical intervention, can cause serious consequences unless repaired. Dural tears are common complications in spine surgery and can range in size from nonleaking pinholes to large defects that require tissue reconstruction with a patch. A persistent tear can lead to severe headaches, CSF fistula, formation of a pseudocyst, nerve root entrapment and fluid collection. Large retrospective series have reported an incidence of 1% for cervical surgeries (Hannallah D, Lee J, Khan M, Donaldson W F, Kang J D: Cerebrospinal fluid leaks following cervical spine surgery. *J Bone Joint Surg Am* 2008; 90(5):1101-1105), and 7.6% and 15.9%, respectively, for primary lumbar and revision lumbar surgeries (Khan M H, Rihn J, Steele G, et al: Postoperative management protocol for incidental dural tears during degenerative lumbar spine surgery: A review of 3,183 consecutive degenerative lumbar cases. *Spine* (Phila Pa. 1976) 2006;31(22):2609-2613).

A watertight closure is the critical factor in repairing the tear. Direct suture repair is routinely used to repair dural tears, but leakage through suture holes can occur. Autologous fat grafts harvested through the same incision have been used to form a hydrophobic seal to prevent leakage. The graft should be sufficiently large to cover the dura and is sutured to the dura adjacent to the defect (Mayfield F H, Kurokawa K: Watertight closure of spinal dura mater: Technical note. *J Neurosurg* 1975; 43(5):639-640). Muscle and fascia have also been used as patches. The use of autologous tissues, however, can lead to prolonged operating time, blood loss and separate incisions. In addition, the quantity of autologous graft may be inadequate in children. Xenografts and cross-linked animal-derived collagen matrices can be used as dural patches, but carry the risk of disease transmission.

Adjunct techniques to assist in sealing the dural tear include fibrin glue and hydrogels. Fibrin glue is prepared from pooled blood and has the potential to transmit disease. At this time, the application of fibrin glue to seal dural tears constitutes off label use. Synthetic hydrogels such as the DuraSeal Spine Sealant System (Confluent Surgical Inc., Waltham, Mass.) consist of two components (polyethylene glycol ester and trilysine amine) and a delivery system which polymerize at the defect site to form a seal. As the hydrogel swells to up to 50% in size during polymerization, neural compression may occur.

Post-operative fibrosis, also referred to as scar tissue formation or post-operative adhesion, is a natural occurrence following various surgical procedures. This natural wound healing cascade in most instances results in the formation of soft tissue adhesions, which either tether, compress, or effect surgical accessibility. Fibrosis is particularly problematic in post-surgical procedures of the spine. For example, peridural fibrosis is the fibroblastic invasion of the nerve roots and peridural sac that are exposed during surgery. The scar tissue can engulf the dura and nerve roots, which can ultimately result in the reoccurrence of symptoms similar to those experienced prior to surgery. Thus, subsequent operations to address the problem may have to be performed, which provides additional inconvenience, costs, and risks to the patient.

Scar formation after spinal surgery can be prevented by the use of membranes and foams applied directly to the spine. Currently, membranes used for adhesion prevention are derived from synthetic type I, II, and III collagen, acellular dermal matrix allograft, HA cellulose film or porcine intestinal submucosa (SIS). These materials possess a variety of disadvantages including poor handling characteristics, undesirable resorption profile, limited fixation capabilities, and limited storage options. Thus, what is needed are grafts that exhibit good adhesion to body tissues and facilitate wound healing yet that do not possess the disadvantages of commercially available options.

SUMMARY

Described herein are tissue grafts derived from the placenta that possess good adhesion to biological tissues and are useful in would healing applications. In one aspect, the tissue graft includes (1) two or more layers of amnion, wherein at least one layer of amnion is cross-linked, (2) two or more layers of chorion, wherein at least one layer of amnion is cross-linked, or (3) one or more layers of amnion and chorion, wherein at least one layer of amnion and/or chorion is cross-linked. In another aspect, the grafts are composed of amnion and chorion cross-linked with one another. In a further aspect, the grafts have one or more layers sandwiched between the amnion and chorion membranes. The amnion and/or the chorion are treated with a cross-linking agent prior to the formation of the graft. The presence of the cross-linking agent present on the graft also enhances adhesion to the biological tissue of interest. Also described herein are methods for making and using the tissue grafts.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
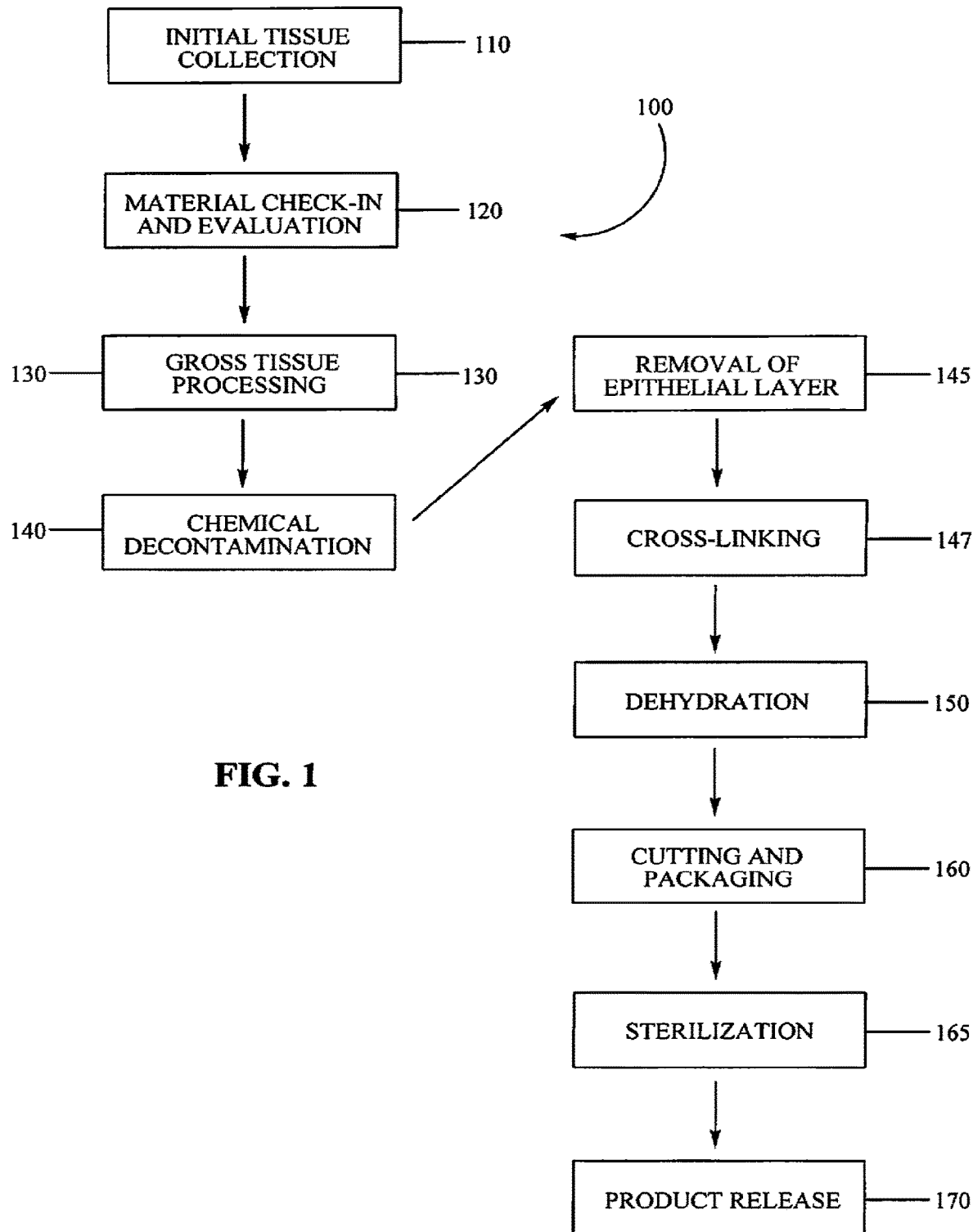
FIG. 1 is an overview flow chart of the process for making the tissue grafts described herein.

Before the present articles and methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a cross-linking agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism.

The term "amnion" as used herein includes amniotic membrane where the intermediate tissue layer is intact or has been substantially removed.

Titles or subtitles may be used in the specification for the convenience of a reader, which are not intended to influence the scope of the present invention. Additionally, some terms used in this specification are more specifically defined below.

I. Tissue Grafts and Methods for Making Thereof

Described herein are tissue grafts derived from the placenta that possess good adhesion to biological tissues and are useful in would healing applications. In one aspect, the grafts are composed of amnion and/or chorion cross-linked with one another. The amnion and/or the chorion are treated with a cross-linking agent prior to the formation of the graft.

In one aspect, the method for making an amnion tissue graft involves:

(a) providing a first amnion having a first surface and a second surface; and (b) laminating a second amnion or chorion having a first surface and a second surface to the second surface of the first amnion, where the first surface of the second amnion or chorion is laminated to the second surface of the first amnion, and wherein the first amnion, second amnion, and/or the chorion are treated with a cross-linking agent prior to lamination.

In another aspect, the method for making a chorion or chorion/amnion tissue graft involves:

(a) providing a first chorion having a first surface and a second surface; and (b) laminating a second chorion having a first surface and a second surface to the second surface of the first chorion, where the first surface of the second chorion is laminated to the second surface of the first chorion, and wherein the first chorion and/or second chorion are treated with a cross-linking agent prior to lamination.

In another aspect, the method for making a the tissue graft involves:

(a) optionally removing substantially all of the epithelium cells of the amnion to expose the basement membrane of the amnion to produce a first membrane having an expose basement membrane and a second surface;

(b) treating the first membrane with a first cross-linking agent; and (c) mounting a chorion having a stromal layer and a second surface to the amnion, wherein the stromal layer of the chorion is adjacent to the second surface of the amnion, wherein the chorion is treated with a second cross-linking agent, and wherein the first cross-linking agent and the second cross-linking agent are the same or different.

In another aspect, the tissue graft is produced by the method involving:

(a) providing a first amnion having a first surface and a second surface; and (b) laminating a second amnion or first chorion having a first surface and a second surface to the second surface of the first amnion, where the first surface of the second amnion or first chorion is laminated to the second surface of the first amnion to produce a laminated article, and (c) contacting the laminated article with a cross-linking agent.

In another aspect, the tissue graft is produced by the method involving:

(a) providing a first chorion having a first surface and a second surface; and (b) laminating a second chorion or first amnion having a first surface and a second surface to the second surface of the first chorion, where the first surface of the second chorion or first amnion is laminated to the second surface of the first chorion to produce a laminated article, and (c) contacting the laminated article with a cross-linking agent.

In a further aspect, the tissue graft is produced by the method involving:

(a) obtaining a placenta from a subject, wherein the placenta comprises an amnion and a chorion;

(b) cleaning the placenta;

(c) separating the chorion tissue layer from the amnion layer, wherein the amnion comprises epithelium cells adjacent to a basement membrane;

(d) optionally removing substantially all of the epithelium cells to expose the basement membrane of the amnion to produce a first membrane:

(e) treating the first membrane and chorion with one or more cross-linking agents;

(f) mounting the first membrane onto a surface of a drying fixture, wherein the basement membrane of the first membrane is adjacent to the surface of the drying fixture;

(g) mounting a chorion on the first membrane to produce the tissue graft; and (h) dehydrating the tissue graft on the drying fixture.

FIG. 1 depicts an exemplary overview (100) and certain aspects of the steps to harvest, process, and prepare placental material for later use as a tissue graft. More detailed descriptions and discussion regarding each individual step will follow. Initially, the placenta tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the amnion and chorion then takes place (step 130). Acceptable tissue is then decontaminated (step 140), followed by the optional step of substantially removing the epithelium layer from the amnion to expose the basement membrane (step 145). Next, the amnion and/or chorion are treated with a cross-linking agent solution (step 147). The tissue graft is then prepared from the amnion and/or chorion and the graft is subsequently dehydrated (step 150), cut and packaged (step 160), sterilized using gamma radiation or electron beam radiation (step 165), and released (step 170) to the market for use by surgeons and other medical professionals in appropriate surgical procedures and for wound care. Each step is described in detail below.

Initial Tissue Collection (Step 110)

The components used to produce the tissue grafts are derived from the placenta. The source of the placenta can vary. In one aspect, the placenta is derived from a mammal such as human and other animals including, but not limited to, cows, pigs, and the like can be used herein. In the case of humans, the recovery of the placenta originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue further are assembled in a staging area in a controlled environment and are prepared for introduction into a controlled environment. In one aspect, the placenta is processed at room temperature. If the controlled environment is a manufacturing hood, the sterile supplies are opened and placed into the hood using conventional sterilization techniques. If the controlled environment is a clean room, the sterile supplies are opened and placed on a cart covered by a sterile drape. All the work surfaces are covered by a piece of sterile drape using conventional sterilization techniques, and the sterile supplies and the processing equipment are placed onto the sterile drape, again using conventional sterilization techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyperisotonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed. This step must be done with adequate care, again, so as not to tear the amnion. The cleaning of the amnion is complete once the amnion is smooth and opaque-white in appearance.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below. Not wishing to be bound by theory, the removal of the intermediate layer can accelerate the drying of the tissue graft, particularly if multiple amnion membranes are used to produce the graft. The intermediate layer can be removed from the amnion prior contacting the amnion with the cross-linking agent or, in the alternative, can be removed after the amnion has been contacted with the cross-linking agent.

Chemical Decontamination (Step 140)

The amnion and chorion isolated above can be chemically decontaminated using the techniques described below. In one aspect, the amnion and chorion is decontaminated at room temperature. In one aspect, the amnion produced in step 130 can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants. If the rocker platform was not in the critical environment (e.g., the manufacturing hood), the Nalgene jar is returned to the controlled/sterile environment and opened. Using sterile forceps or by aseptically decanting the contents, the amnion is gently removed from the Nalgene jar containing the 18% hyperisotonic saline solution and placed into an empty Nalgene jar. This empty Nalgene jar with the amnion is then aseptically filled with a pre-mixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/sterile environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

Optional Removal of Epithelium Layer from Amnion (Step 145)

In certain aspects, it is desirable to remove the epithelium layer present on the amnion. In one aspect, the epithelium layer present on the amnion is substantially removed in order to expose the basement layer of the amnion. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper. Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the before the tissue has been dehydrated as described in the next section. For example, a representative sample graft is removed for microscopic analysis. The tissue sample is place onto a standard slide, stained with Eosin Y and viewed under the microscope. If epithelium is present, it will appear as cobblestone-shaped cells.

The methods described herein, particularly steps 130 and 145, do not remove all cellular components in the amnion. This technique is referred to in the art as "decellularization." Decellularization generally involves the physical and/or chemical removal of all cells present in the amnion, which includes epithelial cells and fibroblast cells. Although step 145 does remove epithelial cells, the fibroblast layer present in the amnion stromal layer is intact, even after removal of the intermediate layer discussed in step 130.

Treatment with a Cross-Linking Agent (Step 147)

Depending upon the application of the tissue graft, the amnion and/or chorion are individually treated with a cross-linking agent prior to lamination. In another aspect, a laminate composed of (1) two or more layers of amnion, (2) two or more layers of chorion, or (3) one or more layers of amnion and chorion can subsequently be treated with a cross-linking agent after lamination.

In general, the cross-linking agent is nontoxic and non-immunogenic. When the chorion and amnion are treated with the cross-linking agent, the cross-linking agent can be the same or different. In one aspect, the chorion and amnion can be treated separately with a cross-linking agent or, in the alternative, the chorion and amnion can be treated together with the same cross-linking agent. In certain aspects, the amnion or chorion can be treated with two or more different cross-linking agents. The conditions for treating the amnion and/or chorion can vary. In one aspect, the amnion or chorion can be placed in a container holding an aqueous solution of the cross-linking agent. In one aspect, the concentration of the cross-linking agent is from 0.1 M to 5 M, 0.1 M to 4 M, 0.1 M to 3 M, 0.1 M to 2 M, or 0.1 M to 1 M. In another aspect, the amnion or chorion are treated with the cross-linking agent for 1 to 2 seconds up to 60 minutes. In a further aspect, the amnion or chorion are treated with the cross-linking agent at room temperature up to 50° C.

The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehydes such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy] succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, di succinimidyl suberate, and 1-ethyl-3-[3-dimethylaminopropyl]carbodiimide hydrochloride, a bifunctional oxirane (OXR), or ethylene glycol diglycidyl ether (EGDE).

In one aspect, sugar is the cross-linking agent, where the sugar can react with proteins present in the amnion and chorion to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerose, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof. Thus, in one aspect, the amnion or chorion include at least one cross-linker covalently attached to the membrane. In another aspect, a tissue graft includes an amnion and a chorion laminate, wherein the amnion and chorion are covalently attached to one another via a cross-linker.

The following procedure provides an exemplary method for treating the amnion and chorion with a cross-linking agent. The cleaned and decontaminated chorion and amnion are placed on the sterile field in the manufacturing hood. The tissue is transferred to a Nalgene jar containing a cross-linking agent, preferably 0.05 to 1 M D-ribose, preferably 0.2 M (3.01%) D-ribose, for 1 to 60 minutes, preferably 5 minutes. The tissues may be treated with the cross-linking agent either in separate containers or together in the same container. After the incubation, the tissue is removed from the solution and, optionally, allowed to dry.

Preparation of Tissue Graft and Dehydration (Step 150)

After the amnion and/or chorion have been treated with the cross-linking agent individually or as a laminate as discussed in the previous section, a tissue graft composed of the amnion and/or chorion is produced and subsequently dehydrated. In one aspect, the tissue graft is a laminate composed of two or more amnion, two or more chorion, or amnion and chorion layered on top of each other. In one aspect, the tissue graft is dehydrated by chemical dehydration followed by freeze-drying. In one aspect, the chemical dehydration step is performed by contacting the amnion and chorion independently or as a laminate with a polar organic solvent for a sufficient time and amount in order to substantially (i.e., greater than 90%, greater than 95%, or greater than 99%) or completely remove residual water present in the amnion or chorion (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below.

After chemical dehydration, the tissue graft is freeze-dried in order to remove any residual water and polar organic solvent. In one aspect, the amnion and chorion can be laid on a suitable drying fixture prior to freeze-drying. In one aspect, amnion treated with a cross-linking agent is laid on a suitable drying fixture, where the exposed basement (i.e., epithelium layer substantially removed) or unexposed basement membrane (i.e., epithelium layer not removed) is adjacent to the surface of the drying fixture.

In one aspect, additional amnion membrane(s) (cross-linking agent-treated or untreated) can be applied to the first amnion affixed to the drying fixture prior to application of the chorion (treated or untreated with cross-linking agent). In these aspects, it is not necessary to remove the epithelial cells from the basement membrane for those layers that are not in direct contact with host cells. Although in this aspect, the fibroblast layer is used to adhere the membranes together, other techniques and materials such as, for example, fibrin glue, gelatin, photochemical techniques, and suturing can be used to produce the multi-laminated tissue graft. The actual number of layers will depend upon the surgical need and procedure with which the tissue graft is designed to be used for. In general, the tissue grafts described herein are cut to size to match the morphology of the wound, placed on or within the wound, and if desired, can be held in place with sutures or surgical adhesives to augment the cross-linking agent.

In other aspects, the amnion can be placed on the surface of the drying fixture such that the exposed basement or unexposed basement membrane is facing up. In certain aspects, one or more additional membranes can be laminated between the amnion and chorion membranes. In this aspect, the additional membrane(s) can optionally be treated with a cross-linking agent. Examples of additional membranes include, but are not limited to, allograft pericardium, allograft acelluar dermis, amnion, chorion, Wharton's jelly, purified xenograft Type-1 collagen, biocellulose polymers or copolymers, biocompatible synthetic polymer or copolymer films, purified small intestinal submucosa, bladder acellular matrix, cadaveric fasia, or any combination thereof, wherein any of the membranes can optionally be treated with a cross-linking agent.

The drying fixture is preferably sized to be large enough to receive the amnion and chorion, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue can also be used for the drying fixture.

Figure 2:
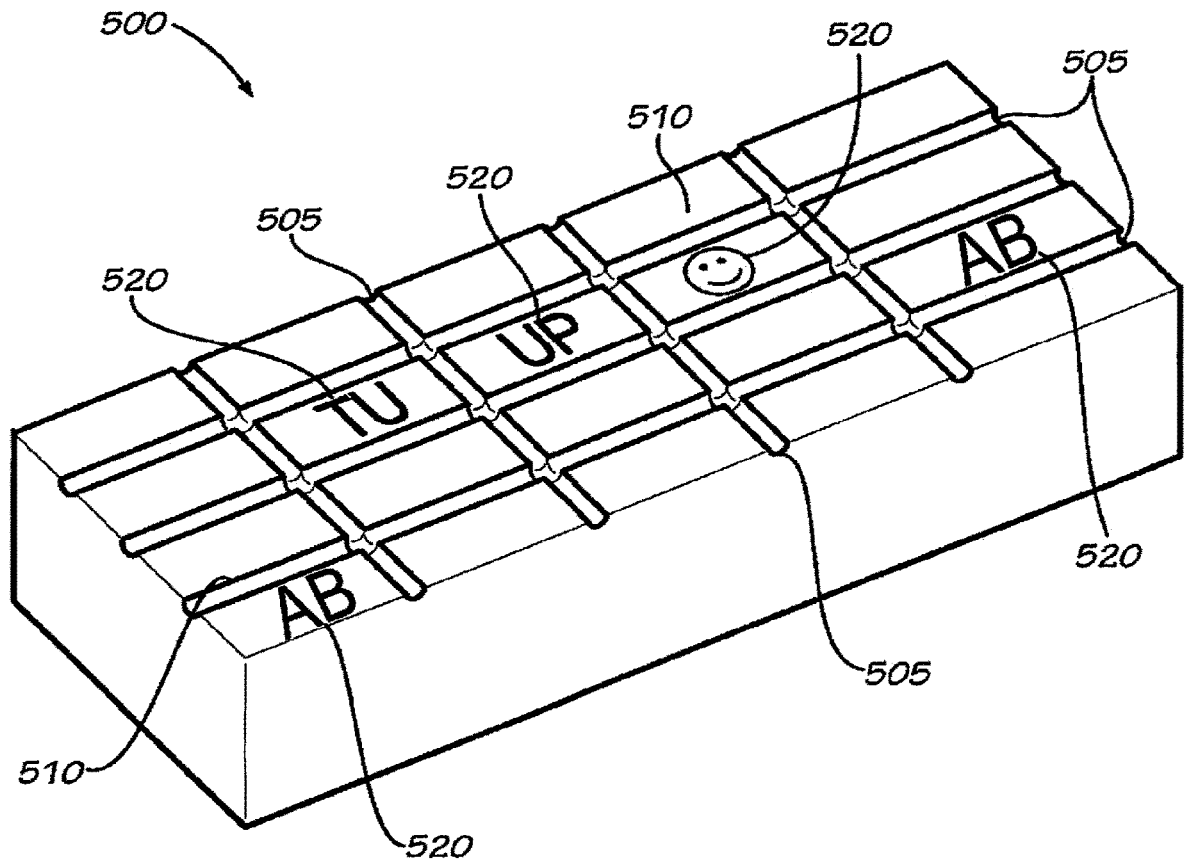
FIG. 2 is a perspective view of an exemplary drying fixture for making the tissue grafts described herein.

In one aspect, similar to that shown in FIG. 2, the receiving surface of the drying fixture 500 has grooves 505 that define the product spaces 510, which are the desired outer contours of the tissue after it is cut and of a size and shape that is desired for the applicable surgical procedure in which the tissue will be used. For example, the drying fixture can be laid out so that the grooves are in a grid arrangement. The grids on a single drying fixture may be the same uniform size or may include multiple sizes that are designed for different surgical applications. Nevertheless, any size and shape arrangement can be used for the drying fixture, as will be appreciated by those skilled in the art. In another embodiment, instead of having grooves to define the product spaces, the drying fixture has raised ridges or blades.

Within the "empty" space between the grooves or ridges, the drying fixture can include a slightly raised or indented texture in the form of text, logo, name, or similar design 520. This textured text, logo, name, or design can be customized. When dried, the tissue will mold itself around the raised texture or into the indented texture—essentially providing a label within the tissue itself. Preferably, the texture/label can be read or viewed on the tissue graft in only one orientation so that, after drying and cutting, an end user (typically, a clinician) of the dried tissue will be able to tell the stromal side from the basement side of the dried tissue. The reason this is desired is because, during a surgical procedure, it is desirable to place the allograft in place, with amnion basement side down or adjacent the native tissue of the patient receiving the allograft. FIG. 2 illustrates a variety of marks, logos, and text 520 that can be included within the empty spaces 510 of the drying fixture 500. Typically, a single drying fixture will include the same design or text within all of the empty spaces; however, FIG. 2 shows, for illustrative purposes, a wide variety of designs that can be included on such drying fixtures to emboss each graft.

Once the tissue graft composed of amnion and/or chorion is placed on the drying fixture, the drying fixture is placed in the freeze-dryer. The use of the freeze-dryer to dehydrate the tissue grafts can be more efficient and thorough compared to other techniques such as thermal dehydration. In general, it is desirable to avoid ice crystal formation in the placental tissue grafts as this may damage the extracellular matrix in the tissue graft. By chemically dehydrating the amnion and chorion prior to freeze-drying, this problem can be avoided.

In another aspect, the dehydration step involves applying heat to the tissue graft. In one aspect, the amnion and/or chorion is laid on a suitable drying fixture as discussed above, and the drying fixture is placed in a sterile Tyvex (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 to 120 minutes. In one aspect, the heating step can be performed at 45 minutes at a temperature of approximately 45 degrees Celcius to dry the tissue sufficiently but without over-drying or burning the tissue graft. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

Figure 3:
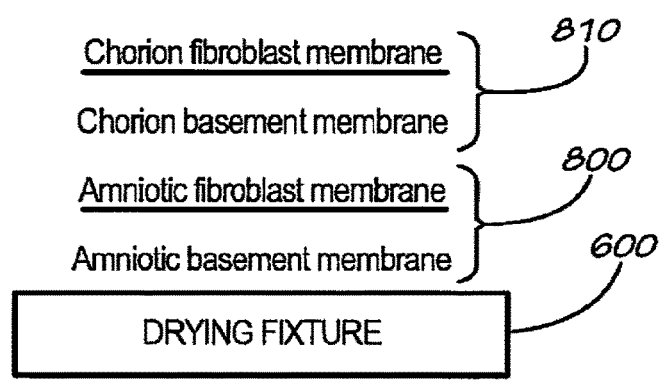
FIG. 3 is a side view of an amnion/chorion tissue graft described herein.
Figure 4:
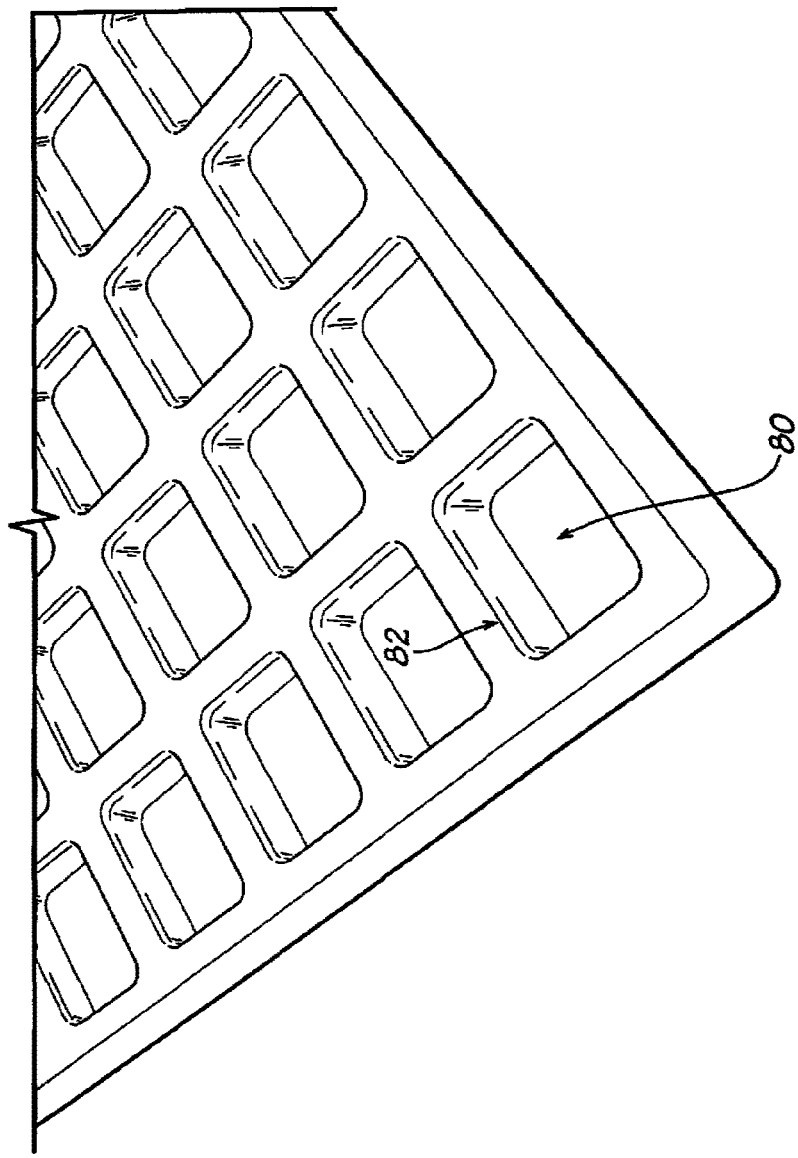
FIG. 4 shows an exemplary drying fixture and drying rack useful in preparing tissues grafts described herein.

In one aspect, after the layer of amnion with the exposed basement (i.e., epithelium layer substantially removed) or unexposed basement membrane (i.e., epithelium layer not removed) has been applied to the drying fixture, the chorion (untreated or treated with a cross-linking agent) is applied to the amnion. In one aspect, the exposed basement layer or unexposed basement layer of the amnion is applied to the drying fixture, and the chorion membrane (treated or untreated with cross-linking agent) is subsequently applied to the amnion affixed to the drying fixture. This aspect is depicted in FIG. 3, where the amnion layer 800 is applied to drying fixture 600, and chorion layer 810 is applied to amnion layer 800. In other aspects, once the amnion (and other membranes described below) and chorion have been applied to the drying fixture, a drying frame can be applied over membranes. This feature is depicted in FIG. 4, where the drying rack 82 is placed on top of drying fixture 80. The drying frame holds the membranes in place. Additionally, the drying frame allows the entire sheet of tissue graft to dry completely without lifting, which results in increased yields.

In certain aspects the tissue graft is not physically altered except for final cutting and packaging (step 160). When completed, the processed tissue graft has a semi-transparent appearance with a whitish coloration. The tissue graft is pliable to withstand bending and sizing in its dry, non-hydrated state. The tissue grafts described herein can be stored at room temperature for extended periods of time.

Cutting & Packaging (Step 160)

Once the graft has been adequately dehydrated, the tissue graft is then ready to be cut into specific product sizes and appropriately packaged for storage, terminal sterilization, and later surgical use. In one aspect, the Tyvek bag containing the dehydrated tissue is placed back into the sterile/controlled environment. The number of grafts to be produced is estimated based on the size and shape of the tissue on the drying fixture(s). An appropriate number of pouches, one for each tissue graft, is also introduced into the sterile/controlled environment. The drying fixture(s) are then removed from the Tyvek bag.

If the drying fixture has grooves, then the following exemplary procedure can be used for cutting the tissue graft into product sizes. If the drying fixture is configured in a grid pattern, a #20 or similar straight or rolling blade is used to cut along each groove line in parallel. Next, all lines in the perpendicular direction are cut. Alternatively, if the drying fixture has raised edges or blades, then the following procedure can be used for cutting the tissue graft into product sizes. A sterile roller is used to roll across the drying fixture. Sufficient pressure must be applied so that the dehydrated tissue graft is cut along all of the raised blades or edges of the drying fixture.

After cutting, each tissue graft is placed in a respective "inner" pouch. The inner pouch, which preferably has a clear side and an opaque side, should be oriented clear side facing up. The tissue graft is placed in the "inner" pouch so that the texture in the form of text, logo, name, or similar design is facing out through the clear side of the inner pouch and is visible outside of the inner pouch. This process is repeated for each separate tissue graft.

Each tissue graft is then given a final inspection to confirm that there are no tears or holes, that the product size (as cut) is within approximately 1 millimeter (plus or minus) of the specified length and width size and within approximately 250 microns (plus or minus) thick for that particular graft, that there are no noticeable blemishes or discoloration of the tissue graft, and that the textured logo or wording is readable and viewable through the "inner" pouch.

To the extent possible, oxygen is removed from the inner pouch before it is sealed. The inner pouch can be sealed in any suitable manner; however, a heat seal has shown to be effective. In one aspect, after packaging, the product is terminally sterilized by radiation, using gamma or electron beam sterilization with a target dose of, for example, 17.5 kGy. Next, each inner pouch is separately packaged in an "outer" pouch for further protection, storage, and shipment.

It should be noted that none of the steps described above involve freezing the tissue graft to kill unwanted cells, to decontaminate the tissue graft, or otherwise to preserve the tissue graft. The dehydrated tissue grafts described herein are designed to be stored and shipped at room or ambient temperature without need for refrigeration or freezing.

Product Release (Step 170)

Before the tissue graft is ready for shipment and release to the end user, all documentation related to the manufacture, recovery and donor eligibility are reviewed and deemed acceptable by the quality assurance department and the medical director.

Appropriate labeling and chain of custody is observed throughout all of the above processes, in accordance with accepted industry standards and practice. Appropriate clean room and sterile working conditions are maintained and used, to the extent possible, throughout the above processes.

II. Applications of Tissue Grafts

Due to the enhanced adhesive nature of the tissue grafts described herein, the grafts can be used in numerous medical applications involving wound healing in a subject. Not wishing to be bound by theory, the cross-linking groups covalently attached to the tissue graft can facilitate the non-enzymatic cross-linking of proteins within the graft such as, for example, collagen, and other proteins present in a biological tissue. In one aspect, tissue grafts described herein can cross-link (i.e., form a covalent bond) with dura matter. In other aspects, the tissue grafts described herein can adhere to tendons, ligaments, muscle, and other body tissue. The tissue grafts described herein are useful in the reinforcement and sealing of tears as well as the prevention or reduction of scar formation after surgery in addition to other post-surgical complications. Additionally, due to the enhanced adhesive properties of the tissue graft, the grafts are ready for application to the surgical site without the need for sutures.

In one aspect, the grafts described herein are useful in enhancing or improving wound healing. The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. For the most part, physicians heal these patients without incident. However, physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one aspect, the grafts described herein can function as a tissue regeneration template that delivers essential wound healing factors, extracellular matrix proteins and inflammatory mediators to help reduce inflammation, enhance healing, and reduces scar tissue formation.

In another aspect, the tissue grafts described herein are useful for addressing or alleviating complications to the spine and surrounding regions that occur after surgery. Acute and chronic spinal injuries and pain can be attributed to trauma and/or degenerative changes in the spinal column. For the degenerative patient, there is usually a progression of possible surgeries depending on the patient's symptoms and disease state. The first surgical option when conservative therapy has failed is a laminectomy or micro-discectomy. These minimally invasive procedures are intended to relieve the pain generator or stenosis of the spinal canal. If there is progression of the disease, then other surgeries may be necessary including, but not limited to, a spinal fusion. Spinal fusions may be achieved through several approaches: anterior (from the front through the abdomen), posterior (from the back), or lateral (through the side). Each approach has advantages and disadvantages. The goal is typically to remove the spinal disc, restore disc height and fuse the two spinal vertebrae together to limit motion and further degradation. There are also surgical options for the surgeon and patient to replace the spinal disc with an artificial disc. Spine trauma is typically treated by fusing the spine levels or if a vertebrae is crushed, the surgeon may choose to do a corpectomy and fusing across the levels that were affected.

In one aspect, the tissue grafts described herein are useful in preventing or reducing scar formation on the spine or near the spine and sealing dural tears. Scar formation at or near the spine after surgery can be very debilitating and possibly require subsequent operations to address the symptoms as discussed above. The term "anti-adhesion" is also used in the art to refer to the prevention of scar tissue at or near the spine. In other aspects, the tissue grafts described herein can be used as a protective barrier, where the graft protects the spinal dura from post-surgical trauma from the surrounding surgical site. For example, the grafts can prevent damage to the spinal dura caused by sharp edges from newly cut bone such as vertebrae. In other aspects, the tissue grafts can be used for anterior lumbar interbody fusion, posterior lumbar interbody fusion trans-lumbar interbody fusion, anterior cervical discectomy and fusion, micro discectomy, spinal dura repair, and as a dura sealant to prevent CSF leakage.

Depending upon the surgical procedure, the tissue graft can be applied directly to the spinal dura, the surrounding region of the spine to include nerve roots, or a combination thereof. Due to the unique structure of vertebrae, the tissue graft can be cut into any shape or dimension so that it can be placed and affixed at the appropriate position in the subject. For example, when the tissue graft is used for bi-lateral coverage, membranes in the shape of a rectangle allow the tissue graft to fit around the posterior spinal process, which minimizes lateral movement. In addition to minimizing lateral movement, the tissue graft can also provide proximal and distal barrier coverage where the spinal lamina has been removed for exposure to the affected area. In one aspect, to ensure proper placement, the graft can be embossed on the exposed basement membrane of the graft to ensure proper placement of the graft in the subject. In particular, proper graft placement will ensure that the basement membrane of the graft is in direct contact with the spinal dura or surrounding region. For example, proper membrane placement and orientation is important when applying the material in spinal applications where a posterior or anterior approach is utilized.

The grafts are useful in preventing or reducing scar formation that can result from a variety of surgical procedures associated with the spine. The grafts can be used after any procedure in the neck, mid-back, or lower back. Depending upon the application, the epithelium of the amnion membrane can be substantially removed. For example, in posterior procedures such as a laminectomy or discectomy, the epithelium layer is substantially removed. Removal of the epithelial cell layer exposes the amnion's basement membrane layer, which increases cell signaling characteristics. This up regulation response enhances cellular migration and expression of anti-inflammatory proteins, which inhibits fibrosis. The spinal dura is typically left unprotected following posterior procedures. Thus, the grafts described herein provide an unmet need in these procedures.

In other aspects, the epithelial cell layer is not removed. For example, in anterior procedures or modified anterior procedures such as Anterior Lumbar Interbody Fusion (ALIF) and Transforaminal Interbody Fusion (TLIF), the amnion epithelium layer is not removed and remains intact. In these aspects, the grafts provide additional protection to the vertebral surgical site by maintaining separation from the peritoneum, larger vessels, and abdominal musculature. The membrane serves as a reduced friction anatomical barrier against adhesions and scaring. For example, the grafts can prevent scar tissue binding major blood vessels to the spine. This is a common problem with post-spinal surgery, which requires a second surgical procedure to address this.

In another aspect, the tissue grafts are useful in dental applications. For example, the grafts can be used around dental implants or in the treatment of advanced gingival recession defect. In another aspect, the grafts can be used in guided tissue regeneration.

In other aspects, the grafts described herein can be used in orthopedic applications (i.e., sports medicine). Sports medicine includes the repair and reconstruction of various soft-tissue injuries in or around joints caused by traumas, or chronic conditions brought about by repeated motion, in active individuals and athletes. For example, sports medicine includes the treatment of a variety of different injuries associated with, but not limited to, shoulders, elbows, feet, ankles hand and wrists.

The main types of injuries include tendon and ligament sprains and ruptures in the various joints, with the most common being ACL in the knee and rotator cuff in the shoulder. Non-tendon and ligament procedures include repair of torn knee meniscus and repair of knee cartilage which if left un-treated can lead to osteoarthritis of the joint. Non-surgical options also include injections of anti-inflammatory drugs to inflamed tendons (such as "tennis elbow"), injection of lubricants into joints (such as hyaluronic acid into the knee), as well as physiotherapy and bracing.

In one aspect, the tissue grafts described herein can be used to wrap tendon repairs to prevent scar formation on the healing tendon. They can also provide a protective, enclosed environment for the repair to progress successfully. The tissue grafts can be used as an off-the-shelf tendon and ligament to replace the need to purchase an allograft or perform tendon or ligament transfer.

In other aspects, the tissue grafts described herein can be used in the reinforcement of rotator cuffs. Some rotator cuff tears are large enough that they require a reinforcement matrix to support the repair due to lack of viable native tissue. The tissue grafts described herein can be used as a matrix to reinforce a repair. In one aspect, the tissue grafts described herein can be used to repair knee cartilage. For example, the tissue grafts can be used as a barrier to hold cell cultured chondrocytes or other pro-cartilage regeneration matrix inside a chondral defect. In this aspect, the tissue graft would be utilized as a flap to close the defect and hold the matrix in place.

In one aspect, the tissue grafts can be used to repair peripheral nerves. The tissue graft can be used as a wrap on nerve repairs to prevent scar formation onto the healing nerve. The tissue graft can also provide a protective enclosed environment for the repair to progress successfully. In other aspects, the tissue grafts can be manufactured into a nerve regeneration tube to guide nerve growth in a protective environment where the nerve ends cannot be re-approximated. Here, nerves can re-attach up to a certain distance if the ends are allowed to meet freely without other soft tissue interfering. In another aspect, the tissue graft can be used to wrap nerve bundles after prostatectomy procedures. These nerves are responsible for erectile function and possible continence. The tissue grafts can be laid on the nerves to keep them from scarring and possibly damaging the nerves.

In other aspects, the tissue grafts described herein can be used in other orthopedic applications such as aid in the repair of periostium; help repair ruptured/damaged bursa; help secure void filling material during bone repair; or in applications involving a subject's extremities (e.g., anti-adhesion barrier for small bone fixation, anti-adhesion barrier where metal plating or hardware is used, or help repair ruptured/damaged bursa).

In another aspect, the tissue grafts can be used in obstetrics and gynecological (OB/GYN) surgical procedures involving the treatment of diseases that may be related to the fertility of the female, pain caused by the reproductive system or cancer in the reproductive system. These procedures include the removal of uterine fibroids (myomectomy), removal of ovarian cysts, tubal ligations, endometriosis treatments, removal of some cancerous or non-cancerous tumors, and vaginal slings. These procedures may be completed through a transvaginal, abdominal or laproscopical approach.

The tissue grafts can be used as a patch to reduce the amount of scar tissue in the reproductive system after a surgical procedure. Scar tissue is another form of fibrous tissue and may also contribute to fertility problems. The ability to minimize the amount of scar on the ovaries, or within the fallopian tubes may help with post-operative fertility and even pain. In another aspect, the tissue grafts can be used to reline the uterine wall after severe endometriosis treatments and increase the patient's ability to conceive. In a further aspect, the tissue graft can be used as an anti-adhesion barrier after removal of ovarian cyst or aid in the repair of vaginal wall erosion.

In other aspects, the tissue grafts can be used in cardiac applications. Angina is severe chest pain due to ischemia (a lack of blood, thus a lack of oxygen supply) of the heart muscle, generally due to obstruction or spasm of the coronary arteries (the heart's blood vessels). Coronary artery disease, the main cause of angina, is due to atherosclerosis of the cardiac arteries. Various open cardiac and vascular surgery procedures to remove atherosclerotic clots require the repair, reconstruction and closure of the vessel, and the support of a regenerative tissue patch to close and patch the surgical defect. Heart by-pass grafts and heart defect reconstruction (as part of an open-heart surgical procedure) also can benefit from a patch or graft to provide a buttress to soft-tissue weakness, tissue replacement if there is a lack of suitable tissue, and also the potential to reduce adhesions to the heart itself. The tissue grafts described herein can be used as a patch to support the repair of vascular and cardiac defects caused by operations and complications such as carotid artery repair, coronary artery bypass grafting, congenital heart disease, heart valve repair, and vascular repair (i.e. peripheral vessels). The tissue grafts described herein can be used in general surgery procedures.

For example, general surgical procedures include procedures related to the abdominal cavity. These include the intestines, stomach, colon, liver, gallbladder, appendix, bile ducts and thyroid glands. Procedures may include hernias, polypectomy, cancer removal, surgical treatment of Crohn's and ulcerative colitis. These procedures may be done open or laparoscopically. In other aspects, the tissue grafts can be used to facilitate closure of anastomosis, an anti-adhesion barrier for anastomosis, or an anti-adhesion barrier for hernia repair.

In other aspects, the tissue grafts can be used in ENT procedures. Tympanoplasty is performed for the reconstruction of the eardrum (tympanic membrane) and/or the small bones of the middle ear. There are several options for treating a perforated eardrum. If the perforation is from recent trauma, many ear, nose and throat specialists will elect to watch and see if it heals on its own. If this does not occur or frequent re-perforation occurs in the same area, surgery may be considered. Tympanoplasty can be performed through the ear canal or through an incision behind the ear. Here, the surgeon harvests a graft from the tissues under the skin around the ear and uses it to reconstruct the eardrum. The tissue grafts described herein can be used to prevent the additional trauma associated with harvesting the patients' own tissue and save time in surgery. In other aspects, the tissue grafts can be used as a wound covering after adenoidectomy, a wound cover after tonsillectomy, or facilitate repair of the Sniderian membrane.

In other aspects, the tissue grafts described herein can be used in plastic surgery procedures. Scar revision is surgery to improve or reduce the appearance of scars. It also restores function and corrects skin changes (disfigurement) caused by an injury, wound, or previous surgery. Scar tissue forms as skin heals after an injury or surgery. The amount of scarring may be determined by the wound size, depth, and location; the person's age; heredity; and skin characteristics including skin color (pigmentation). Surgery involves excision of the scar and careful closure of the defect. In one aspect, the tissue grafts described herein can be used as a patch to aid in the healing and prevention of scars; and keloid or cancer revision/removal where careful approximation of soft-tissue edges is not achievable and scar tissue can result. Additionally, the anti-inflammatory properties of the tissue graft can enhance healing as well.

In other aspects, the tissue grafts can be used in ophthalmological applications (e.g., on-lay grafts ocular surface repair) or urological applications (e.g., facilitate closure of the vas deferens during vasectomy reversal or facilitate closure of the vas deferens resulting from trauma).

In one aspect, the tissue grafts can be used in cranial dura repair and replacement, in the elimination of a frenum pull, the regeneration of lost patella tissue, the repair of the Schneiderian membrane in the sinus cavity, soft tissue around dental implants, vestibuloplasty, and guided tissue regeneration.

Depending upon the application of the graft, the graft can be soaked with a bioactive agent such as a solution composed of naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Here, one or more membrane layers of the tissue graft absorb the bioactive agent. Upon application of the wet tissue graft with bioactive agent to the wound, the bioactive agent is delivered to the wound over time.

Although the tissue grafts described herein can be applied directly to the tissue of a subject, they can also be applied to a wound dressing that can subsequently be applied to the subject. For example, the wound dressing can be gauze, a bandage or wrap, or any other suitable article capable of containing or affixing the tissue graft that can be applied directly to a subject.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A method for enhancing adhesion of a tissue graft to a biological tissue of a patient, said method comprising applying a tissue graft to said biological tissue of a patient, wherein said tissue graft comprises (1) two or more layers of amnion, wherein at least one layer of amnion is treated with a cross-linking agent and comprises a cross-linking group; or (2) one or more layers of amnion and chorion, wherein at least one layer of amnion and/or chorion is treated with a cross-linking agent and comprises a cross-linking group; wherein one or more of said cross-linking groups forms a covalent bond with said biological tissue, thereby enhancing adhesion of the tissue graft to the biological tissue; wherein at least one layer of amnion or chorion has not been treated with a cross-linking agent; wherein the tissue graft comprises a first surface and a second surface, where the first surface is a basement membrane and the second surface is not a basement membrane; and wherein the tissue graft is not decellularized.

2. The method of claim 1, wherein the tissue graft comprises two or more layers of amnion, wherein at least one layer of said amnion is treated with a cross-linking agent, wherein said treated amnion comprises a cross-linking group.

3. The method of claim 1, wherein the tissue graft comprises one or more layers of amnion and one or more layers of chorion, wherein at least one layer of said amnion and/or said chorion is treated with a cross-linking agent, and wherein said treated amnion and/or chorion comprises a cross-linking group.

4. The method of claim 1, wherein more than one layer of amnion and/or chorion is treated with a cross-linking agent and comprises a cross-linking group, and the amnion layers and/or the chorion layers are treated with the same cross-linking agent.

5. The method of claim 1, wherein more than one layer of amnion and/or chorion is treated with a cross-linking agent and comprises a cross-linking group, and the amnion layers and/or the chorion layers are treated with different cross-linking agents.

6. The method of claim 1, wherein the cross-linking agent comprises a sugar, a dialdehyde, a carbodiimide, or a combination thereof.

7. The method of claim 6, wherein the sugar comprises D-ribose, glycerose, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof.

8. The method of claim 1, wherein the tissue graft includes an embossed texture or design.

9. The method of claim 1, wherein the tissue graft comprises one or more additional membranes treated with a cross-linking agent.

10. The method of claim 9, wherein the one or more additional membranes comprise amnion, chorion, allograft pericardium, allograft acellular dermis, amniotic membrane, Wharton's jelly, purified xenograft Type-1 collagen, biocellulose polymers or copolymers, biocompatible synthetic polymer or copolymer films, purified small intestinal submucosa, bladder acellular matrix, cadaveric fascia, or any combination thereof.

11. The method of claim 9, wherein the one or more additional membranes comprise an amnion membrane.

12. The method of claim 1, wherein the biological tissue comprises a wound and said tissue graft is a wound dressing.

13. The method of claim 1, wherein the biological tissue is the spinal dura of the patient or a region near the spine, and the tissue graft is applied after a surgical procedure to prevent or reduce scar formation on or near the spine.

14. The method of claim 13, wherein the surgical procedure comprises a posterior procedure.

15. The method of claim 14, wherein the posterior procedure is a laminectomy, discectomy, a Posterior Lumbar Interbody Fusion, or a Transforaminal Lumbar Interbody Fusion.

16. The method of claim 13, wherein the surgical procedure comprises an anterior procedure.

17. The method of claim 1, wherein the tissue graft is applied to the biological tissue without the use of a suture.

18. The method of claim 1, wherein the biological tissue is the spinal dura of the patient, and the tissue graft is applied after a dural tear.

19. The method of claim 1, wherein the biological tissue comprises a wound and the tissue graft is applied to the wound, wherein the wound is in the cranial dura, a wound resulting from a perioplastic procedure, a frenum pull, lost patella tissue, associated with the Schneiderian membrane in the sinus cavity, or associated with the soft tissue around dental implants, wherein the tissue graft promotes healing of the wound.

20. The method of claim 1, wherein the biological tissue comprises a wound associated with a dental surgical procedure, an orthopedic application, an ENT application, a gynecological application, an urological application, or general surgery, or wherein the biological tissue comprises an extremity having a wound, or wherein the biological tissue comprises an eye.

* * * * *